United States Patent
Willand et al.

(10) Patent No.: US 10,174,050 B2
(45) Date of Patent: Jan. 8, 2019

(54) SPIROISOXAZOLINE COMPOUNDS HAVING AN ACTIVITY POTENTIATING THE ACTIVITY OF AN ANTIBIOTIC

(71) Applicant: Universite de Droit et de la Sante de Lille 2, Lille (FR)

(72) Inventors: Nicolas Willand, Lille (FR); Benoit Deprez, Lille (FR); Alain Baulard, Tournai (BE); Priscille Brodin, Paris (FR); Matthieu Frederik Desroses, Knivsta (SE); Laurence Agouridas-Dutot, Lille (FR)

(73) Assignee: Universite de Droit et de la Sante de Lille 2, Lille (FR)

( * ) Notice: Subject to any disclaimer, the term of this patent is extended or adjusted under 35 U.S.C. 154(b) by 64 days.

(21) Appl. No.: 14/653,675

(22) PCT Filed: Dec. 20, 2013

(86) PCT No.: PCT/EP2013/077706
§ 371 (c)(1),
(2) Date: Jun. 18, 2015

(87) PCT Pub. No.: WO2014/096369
PCT Pub. Date: Jun. 26, 2014

(65) Prior Publication Data
US 2015/0344498 A1 Dec. 3, 2015

(30) Foreign Application Priority Data
Dec. 21, 2012 (FR) ...................................... 12 03549

(51) Int. Cl.
 A61K 45/06 (2006.01)
 A61K 31/435 (2006.01)
 C07D 498/10 (2006.01)
(52) U.S. Cl.
 CPC .......... C07D 498/10 (2013.01); A61K 31/435 (2013.01); A61K 45/06 (2013.01)
(58) Field of Classification Search
 CPC ..... A61K 31/435; A61K 45/06; C07D 498/10
 USPC ................... 514/178, 326; 546/16, 209, 210
 See application file for complete search history.

(56) References Cited

U.S. PATENT DOCUMENTS

| | | | | |
|---|---|---|---|---|
| 6,291,469 B1* | 9/2001 | Fisher | ................... | A61K 31/423 514/278 |
| 6,528,534 B2* | 3/2003 | Fisher | ................... | A61K 31/423 514/376 |
| 6,693,109 B2* | 2/2004 | Fisher | ................... | A61K 31/423 514/278 |
| 7,964,624 B1* | 6/2011 | Cottrell | ................ | C07D 498/10 514/256 |
| 7,985,762 B2* | 7/2011 | Cottrell | ................ | C07D 498/10 514/231.5 |
| 8,338,599 B2 | 12/2012 | Deprez et al. | | |
| 8,440,706 B2* | 5/2013 | Cottrell | ................ | C07D 498/10 514/231.5 |
| 8,772,307 B2* | 7/2014 | Frank | ................... | C07D 498/10 514/278 |
| 8,912,329 B2 | 12/2014 | Schoenmakers et al. | | |
| 8,962,658 B2 | 2/2015 | Deprez et al. | | |
| 9,050,295 B2 | 6/2015 | Fussenegger et al. | | |
| 2006/0094767 A1 | 5/2006 | Tsubouchi et al. | | |
| 2008/0269271 A1* | 10/2008 | Frank | ................... | C07D 498/10 514/278 |
| 2011/0055244 A1* | 3/2011 | Donelli | ..................... | G06F 1/14 707/769 |
| 2015/0225388 A1* | 8/2015 | Willand | ............... | C07D 213/81 514/342 |
| 2015/0307471 A1* | 10/2015 | Willand | ............... | C07D 401/04 514/255.01 |

FOREIGN PATENT DOCUMENTS

| | | |
|---|---|---|
| WO | WO 2006/122770 | 11/2006 |
| WO | WO 2009/091324 A1 | 7/2009 |
| WO | WO 2011/146324 A1 | 11/2011 |
| WO | WO 2014/096378 | 6/2014 |

OTHER PUBLICATIONS

Frank et al (AN 2006:1226327, DN 146:7968, HCAPLUS, abstract of WO 2006122770).*

(Continued)

*Primary Examiner* — Sabiha N Qazi
(74) *Attorney, Agent, or Firm* — Medler Ferro Woodhouse & Mills PLLC

(57) ABSTRACT

The present invention concerns a spiroisoxazoline compound of general formula (I):

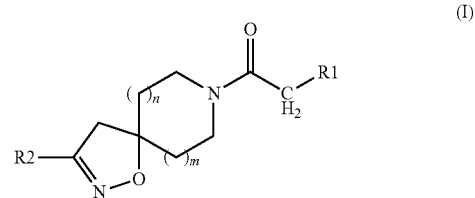

(I)

in which m and n are 0 or 1, R1 represents, inter alia, an optionally substituted alkyl chain, in particular substituted with fluorine or with a cyclic group, and R2 is chosen from phenyl and optionally substituted benzyl, cyclopropyl, cyclobutyl, cyclopentyl, cyclohexyl, and the heterocycles having 5 or 6 vertices comprising at least one atom chosen from S, N and O. The present invention also concerns the use of this compound as a drug, in particular in the treatment of bacterial and mycobacterial infections such as tuberculosis in combination with an antibiotic that is active against bacteria and/or mycobacteria, said compound potentiating the activity of said antibiotic.

15 Claims, No Drawings

(56) References Cited

OTHER PUBLICATIONS

Flipo et al. (Journal of Medicinal Chemistry, 2011, 54, 2994-3010).*
U.S. Appl. No. 14/430,604, Universite de Droit et de la Sante de Lille 2.
Flipo, M., et al., "Ethionamide Boosters: Synthesis, Biological Activity, and Structure-Activity Relationships of a Series of 1,2,4-Oxadiazole EthR Inhibitors," *Journal of Medicinal Chemistry* 54: 2994-3010, The American Chemical Society (2011).
Baulard, A., et al., "Activation of the Pro-drug Ethionamide Is Regulated in Mycobacteria," *J. Biol. Chem.* 275: 28326-28331 (2000).

* cited by examiner

SPIROISOXAZOLINE COMPOUNDS HAVING AN ACTIVITY POTENTIATING THE ACTIVITY OF AN ANTIBIOTIC

The present invention relates to spiroisoxazoline-type compounds for use in the treatment of bacterial and mycobacterial infections, such as for example tuberculosis, leprosy and atypical mycobacterial infections.

The present invention also concerns new compounds that can be used as medicament, in particular as medicament in the treatment of bacterial and mycobacterial infections such as, for example, tuberculosis, leprosy and atypical mycobacterial infections.

The present invention also concerns pharmaceutical compositions comprising, as the active ingredient, at least one of the abovementioned compounds and optionally an antibiotic active against bacteria and/or mycobacteria, notably an antibiotic activatable via the EthA pathway.

The present invention also concerns products (kits) containing at least one of the aforementioned compounds and at least one antibiotic active against bacteria and/or mycobacteria, notably an antibiotic activatable via the EthA pathway as combination products for use simultaneously, separately or spread out in time, in the therapy of tuberculosis, leprosy or general mycobacterial infections.

Tuberculosis kills 2 million people every year in the world. The AIDS epidemics and the emergence of strains that are multi-resistant to antibiotics contribute to exacerbating the impact of this illness, considered by the World Health Organization as responsible for an increasingly dangerous worldwide epidemic and as a health emergency on a global scale.

An increasing number of *Mycobacterium tuberculosis* strains is characterized nowadays by multi-resistance to first-line antibiotics such as isoniazid (INH) and rifampicin (RIF). These antibiotics must then be replaced by second-line antibiotics such as ethionamide (ETH) to which the strains are not resistant but which have the disadvantage of having a low therapeutic index (the therapeutic index of an active ingredient is the ratio of therapeutic dose to toxic dose).

One strategy consisting in increasing the activity of ethionamide (ETH) by associating it to a specific compound has already been considered. In fact. ETH is a prodrug that is transformed in vivo into a therapeutically active form by the EthA enzyme (see the article "Activation of the prodrug ethionamide is regulated in mycobacteria", A. R. Baulard et al., Journal of Biological Chemistry, 2000, 275, 28326-28331). The observed resistances to ETH arise from the fact that the transcriptional repressor EthR of *M. tuberculosis* controls the expression of the EthA enzyme and restricts the transformation of ETH into a therapeutically active substance.

One aim of the present invention is to propose new compounds likely to potentiate the activity of antibiotics active notably against mycobacteria, in particular antibiotics active against mycobacteria and activatable via the EthA pathway, such as for example all the antibiotics of the thioamide family and in particular ethionamide and prothionamide.

Another aim of the present invention is to propose compounds such as previously mentioned that, in combination with an antibiotic active against bacteria and/or mycobacteria, notably an antibiotic active against mycobacteria and activatable via the EthA pathway, and at identical antibiotics dosage, enable a greater efficiency to be achieved or that enable the aforementioned antibiotics dosage to be reduced whilst achieving a given efficiency.

Another aim of the present invention is to propose compounds such as previously mentioned that are simple and inexpensive to produce.

Another aim of the present invention is to propose compounds such as previously mentioned that are satisfactorily soluble in a biologic fluid.

Another aim of the present invention is to propose compounds such as previously mentioned that are likely to be active in particular orally and/or that cause fewer side effects.

To achieve at least one of the aforementioned aims, the present invention thus proposes compounds of the general formula (I):

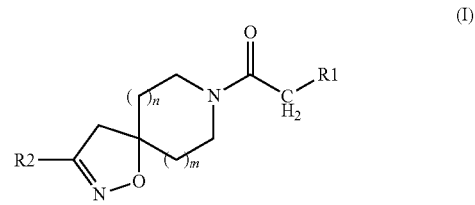

in which:

m=0 or 1;

n=0 or 1;

R1 represents a group chosen from the following groups:

linear or branched C1-C5 alkyl chains;

linear or branched and substituted C1-C5 alkyl chains:
  in particular substituted by at least one fluorine atom (F),
  in particular linear or branched C1-C3 alkyl chains substituted by at least one fluorine atom (F) or by a C3-C6 saturated or unsaturated cyclic group;

C3-C6 saturated or unsaturated cyclic groups; and

CN, $CH_2CN$, $CH_2N_3$ groups:

R2 is chosen from the following groups:

phenyl;

optionally substituted benzyl, in particular benzyl substituted by a Cl or F atom; naphthalenyl;

substituted phenyl, in particular phenyl substituted by at least one linear or branched C1-C4 alkyl chain;

phenyl substituted by at least one linear or branched and substituted C1-C4 alkyl chain, in particular substituted by at least one fluorine atom (F);

phenyl substituted by at least one group chosen from $OCH_3$, $OCF_3$, Cl, F, $CH_3SO_2$ and $CF_3$;

a phenyl group having two consecutive carbon atoms substituted by the same O—$CH_2$—O group;

a cyclopropyl, cyclobutyl, cyclopentyl or cyclohexyl groups; and the heterocycles having 5 or 6 vertices, saturated or unsaturated, comprising at least one atom in the cycle chosen from S, N and O, in particular the aromatic heterocycles having 5 or 6 vertices comprising at least one atom in the cycle chosen from S, N and O.

According to the invention, m and n can be equal to or different from one another. Advantageously, m=n=1. Such components in combination with ethionamide prove particularly active on mycobacteria, in particular on *M. tuberculosis*.

R1 may represent a group chosen from the following groups:

—CH$_2$CF$_3$, —CF$_2$CF$_3$, —(CH$_2$)$_2$CF$_3$, —CH$_2$-isopropyl, cyclopropyl, cyclobutyl, cyclopentyl, cyclopentenyl, —CH$_2$-cyclopropyl, —CH$_2$-cyclobutyl, —CH$_2$-cyclopentyl, optionally substituted phenyl, in particular phenyl substituted by a chlorine (Cl) or fluorine (F) atom, optionally substituted benzyl, in particular benzyl substituted by a Cl or F atom, —O-phenyl and thiophenyl.

The aforementioned substituted R1 groups can be mono-substituted or poly-substituted. According to one embodiment, the aforementioned groups are mono-substituted; the phenyl or benzyl group is then substituted only by a Cl atom or by an F atom. The position of this Cl or F atom is not limited according to the invention, regardless of whether the phenyl or benzyl group is mono-substituted or poly-substituted. Thus, the Cl or F atom can be in ortho, meta or para position relative to the carbon of the benzene cycle bound to the remainder of the molecule having the general formula (I) or relative to the carbon of the benzene cycle bound to the group CH$_2$ bound to the remainder of the molecule having the general formula (I), in the case of a benzyl group.

Advantageously, R1 is chosen from —CH$_2$CF$_3$ and —(CH$_2$)$_2$CF$_3$. These two radicals give the inventive compounds an increased efficiency. It seems that, in particular when R1=CH$_2$CF$_3$, the inventive compound is particularly efficient for increasing the ethionamide's activity on mycobacteria and in particular on *M. tuberculosis*.

According to one embodiment, R2 is chosen from the following groups: phenyl, phenyl groups ortho-substituted by OCH$_3$, OCF$_3$, Cl, F or CF$_3$, in particular substituted in ortho position by OCH$_3$ or Cl. Advantageously, the phenyl groups are mono-substituted in ortho position by a radical chosen from OCH$_3$, OCF$_3$, Cl, F or CF$_3$, in particular mono-substituted in the ortho position by OCH$_3$ or Cl. Such radicals improve the potentiating activity of ethionamide of the inventive compounds. The ortho position of the substituent improves the potentiating activity of ethionamide of the inventive compounds.

According to another embodiment, R2 is chosen from aromatic heterocycles having 5 or 6 atoms, of which at least one atom adjacent to the heterocycle atom bound in alpha position relative to the nitrogen of the cycle

of the compound having the general formula (I) of the invention is a sulfur atom, an oxygen atom or a nitrogen atom. According to the invention, the heterocycles with 5 or 6 atoms can thus comprise two atoms chosen from the atoms S, N and O. In this case, the two atoms chosen from S, N and O can be situated on either side of the heterocycle atom bound to the carbon cycle in alpha of the nitrogen of the cycle

in the formula (I) and directly adjacent to the latter.

The heterocycle atom bound to the aforementioned cycle is advantageously a carbon atom.

Advantageously, R2 is chosen among the following groups:

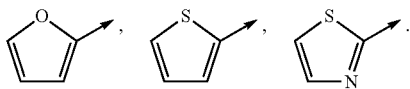

Such compounds are particularly efficient in combination with ethionamide for fighting mycobacteria, in particular *M. tuberculosis*.

According to another embodiment, R2 is chosen from the following groups:

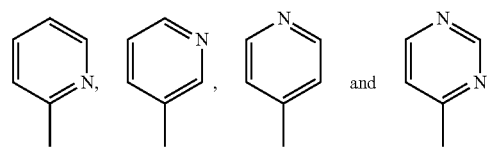

The compound of the invention is advantageously chosen from the following compounds:

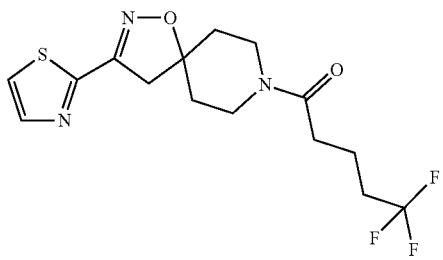

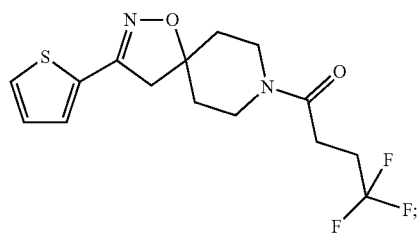

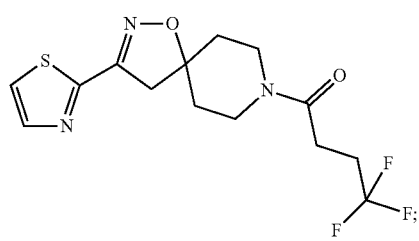

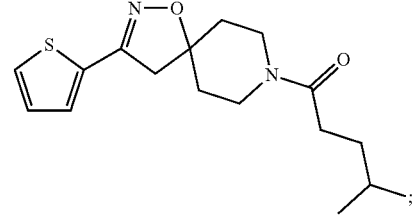

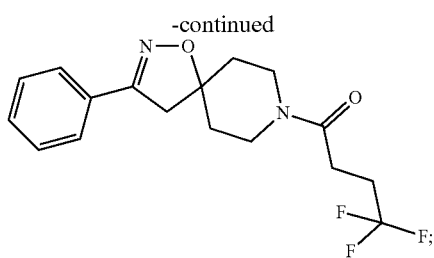
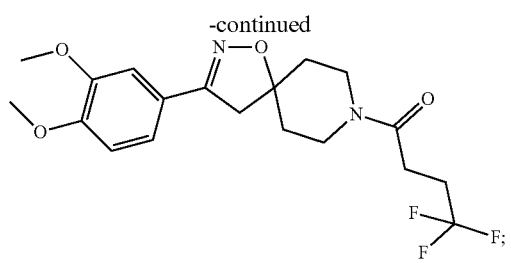
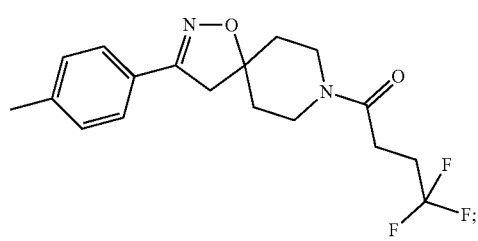
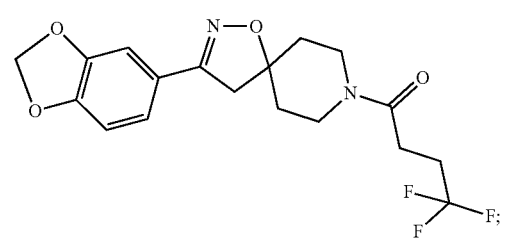
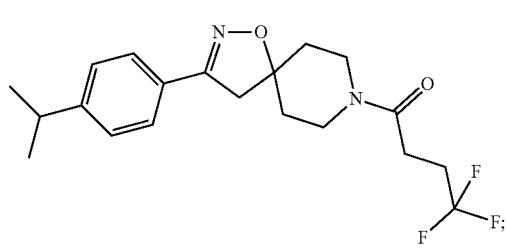
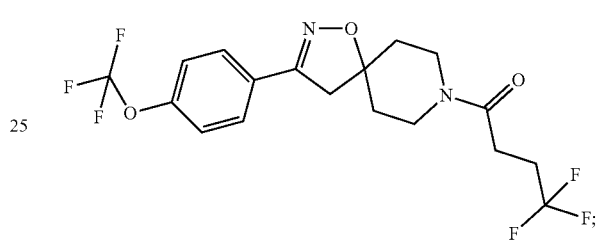
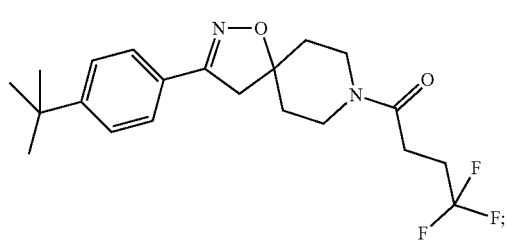
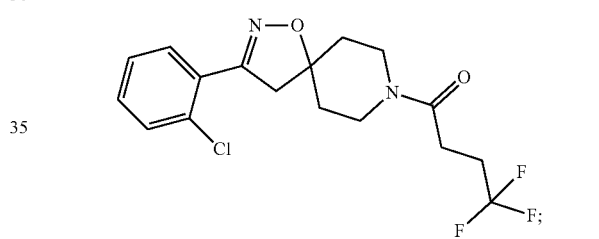
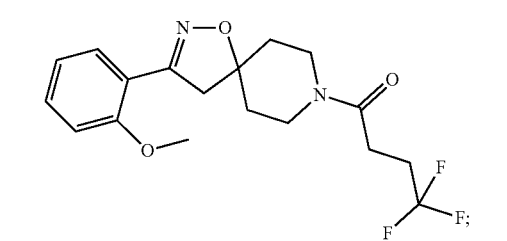
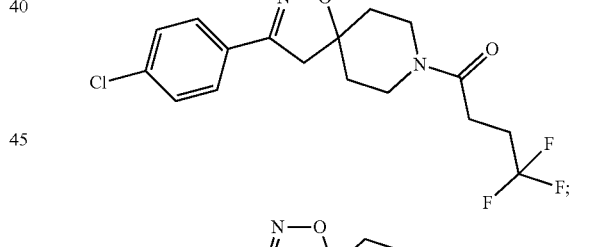
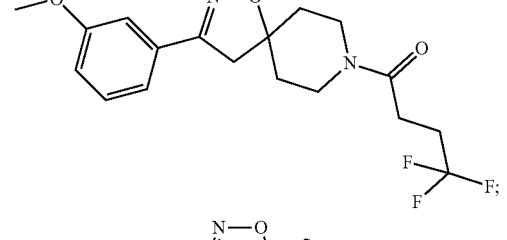
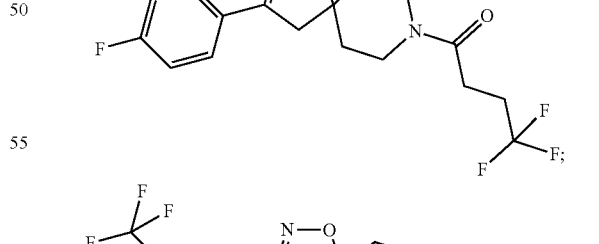
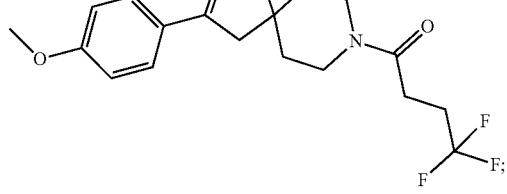
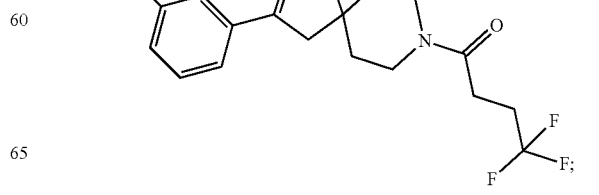

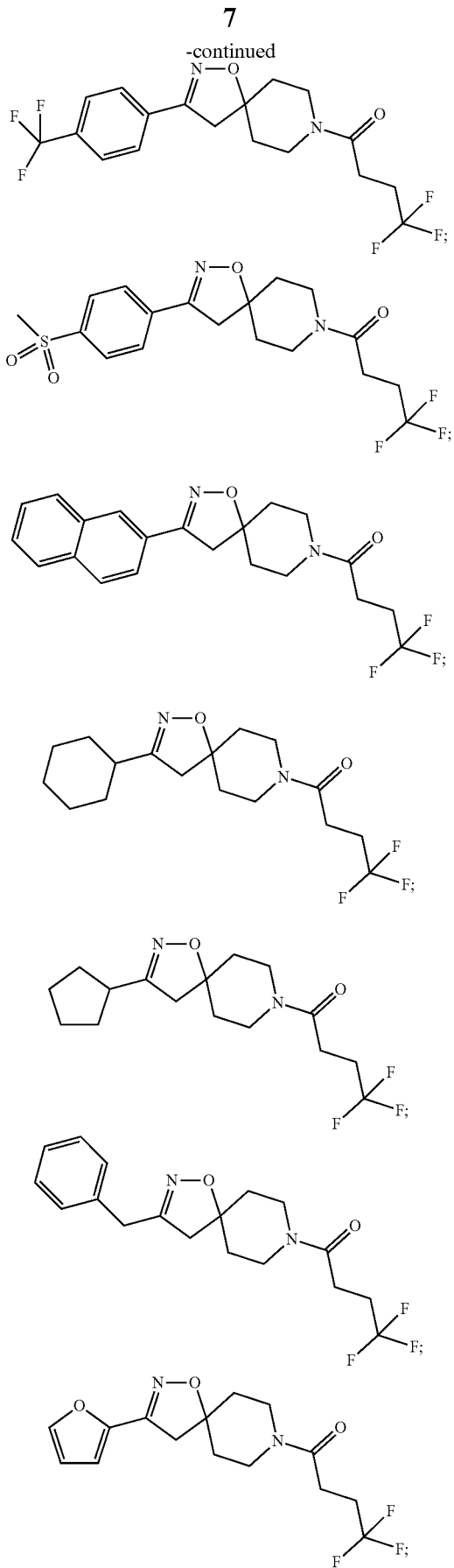

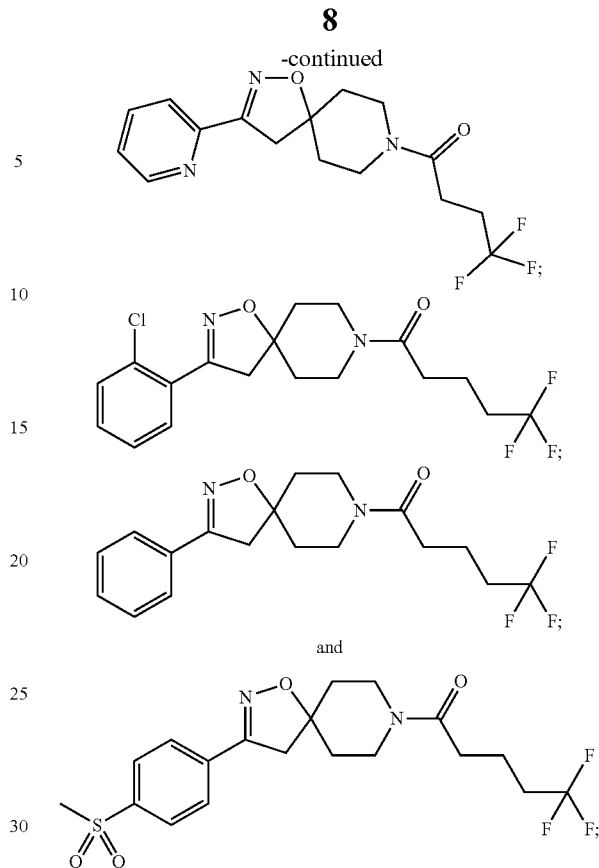

The present invention also concerns the aforementioned compounds for use as medicament, in particular for use in the treatment of bacterial and mycobacterial infections, notably in the treatment of tuberculosis, leprosy or atypical mycobacterial infections.

The present invention also concerns a pharmaceutical composition comprising, as the active ingredient, at least one compound of general formula (I) as previously mentioned and a pharmaceutically acceptable excipient.

Within the pharmaceutical compositions according to the invention, the compound or compounds used as active ingredient(s) can be used in a quantity that enables unit doses to be administered comprised between approximately 0.3 mg and 1 g. Within the pharmaceutical compositions according to the invention, the antibiotic or antibiotics activatable via the enzymatic EthA pathway, when present, are advantageously used in a quantity enabling the administration of unit doses equal to or lower than the doses usually recommended by the World Health Organization (WHO, Treatment of tuberculosis: Guidelines for National Programs. 2003; WHO/CDS/TB2003.313.), national or non-governmental health organizations or the competent pharmaceutical laboratories.

The one skilled in the art is able to choose one or several pharmaceutically acceptable excipients depending on the route of administration of the pharmaceutical composition. The one skilled in the art will of course ensure in doing so that the excipient or excipients used are compatible with the intrinsic properties attached to the composition according to the present invention. Furthermore, the form of the medicament or pharmaceutical composition (for example a solution, a suspension, an emulsion, tablets, capsules, suppositories etc.) will depend on the chosen administration route.

Thus, in the sense of the present invention, the medicament or pharmaceutical composition can be administered by any appropriate route, for example oral, anal, local (topical for example), systemic, intravenous, intramuscular or mucosal route, or else by using a patch, or else in encapsulated form in or immobilized on liposomes, microparticles, microcapsules, associated to nanoparticles and similar. By way of non-limiting examples of excipients suitable for administration by the oral route, one can notably cite talcum, lactose, starch and its derivatives, cellulose and its derivatives, polyethylene glycols, acrylic acid polymers, gelatin, magnesium stearate, animal, vegetal or synthetic fats, paraffin derivatives, glycols, stabilizers, preservatives, antioxidants, wetting agents, anti-caking agents, dispersants, emulsifiers, taste modifying agents, penetrating agents, solubilizing agents etc. The formulation and administration techniques for the medicaments and pharmaceutical compositions are well known in the art here under consideration, the one skilled in the art can notably refer to the work Remington's Pharmaceutical Sciences, latest edition.

The present invention also has the aim of using at least one compound according to the invention for the manufacture of a medicament intended for the prevention and/or treatment of bacterial infections, preferably mycobacterial infections, and more particularly of tuberculosis, leprosy or atypical mycobacterial infections.

Advantageously, the pharmaceutical composition further comprises, as active ingredient, at least one antibiotic active against bacteria and/or mycobacteria, chosen notably from antibiotics activatable via the enzymatic EthA pathway, in particular ethionamide, prothionamide, isoxyl and thioacetazone which are examples of antibiotics activatable via the EthA pathway. However, the invention is not limited to these antibiotics.

The present invention also concerns a kit or product containing at least one compound of formula (I) and at least one antibiotic active against bacteria and/or mycobacteria chosen notably from antibiotics activatable via the enzymatic EthA pathway as combination products for use, simultaneously, separately or spread out in time, in the therapy of tuberculosis, leprosy or general mycobacterial infections.

DEFINITIONS

Within the meaning of the present invention, the thiophenyl group is defined as a cyclic group comprising 4 carbon atoms and one sulfur atom.

When it is not indicated that a group is substituted, the latter is not substituted, within the meaning of the present invention.

When the position of the substituent Is not indicated, the term substituted phenyl concerns any phenyl group of which at least one atom of hydrogen is replaced by a group or an atom such as indicated. Preferably, for R2, the phenyl group is mono-substituted, preferably mono-substituted by a group $OCH_3$, a chlorine atom or a fluorine atom. It can however comprise at least two substituents.

The ortho position of the substituent borne by the phenyl refers to the carbon atom of the phenyl group that is bound to the carbon atom in alpha position relative to the nitrogen of the cycle

of the inventive compounds.

The heterocycles with 5 or 6 atoms can be saturated or unsaturated. They can comprise one or several double bonds. They can also be aromatic cycles. Thus, within the meaning of the present invention, the terms aromatic heterocycles with 5 or 6 vertices comprising at least one atom chosen from N, O and S in the cycle comprise notably aromatic heterocycles with 5 or 6 vertices comprising at least one nitrogen atom in the cycle and only one or several N atoms as heteroatom in the cycle, aromatic heterocycles with 5 or 6 vertices, in particular with 5 vertices, comprising at least one O atom in the cycle and only one or several O atoms as heteroatom(s) in the cycle, aromatic heterocycles with 5 or 6 vertices comprising at least one S atom in the cycle and only one or several S atoms as heteroatom(s) in the cycle, aromatic heterocycles with 5 or 6 vertices, in particular with 5 vertices, comprising at least one nitrogen atom in the cycle and/or at least one O or S atom in the cycle as heteroatoms. In particular, the aromatic heterocycles with 5 or 6 vertices comprising two different or identical heteroatoms chosen from S, N and O belong to aromatic heterocycles with 5 or 6 vertices according to the invention.

Atypical mycobacterial infections are defined here as mycobacterial infections caused by at least one *mycobacterium* other than *M. Tuberculinum* and in particular mycobacterial infections involving *M. Kansasii*.

According to the present invention, the term "treatment" designates the curative treatment and/or prophylactic treatment of the aforementioned infections. The term "treatment" includes all improvement of the patient's state, in particular any diminution of the number of bacteria present in at least one infection site of the patient.

In the present invention, an antibiotic activatable via the EthA pathway is defined as any substance that at least in vitro reacts with the EthA enzyme to produce a substance having antibiotic properties. The one skilled in the art is able to determine if an antibiotic is activatable by the EthA pathway for example by applying the method described in the following publication: "Activation of the prodrug ethionamide is regulated in mycobacteria" A. R. Baulard et al., Journal of Biological Chemistry, 2000, 275, 28326-28331.

Within the meaning of the present invention, an antibiotic active against bacteria and/or mycobacteria is defined as any agent capable of limiting or reducing at least in vitro the proliferation of a bacterium and/or of a *mycobacterium*, in particular *M. tuberculosis*. An agent capable of destroying, at least in vitro, a *mycobacterium*, notably *M. tuberculosis*, is also an antibiotic active against mycobacteria within the meaning of the present invention. Among the antibiotics active against mycobacteria and activatable via the enzymatic EthA pathway, ethionamide, prothionamide, isoxyl, thiacetazone and the mixtures of at least two of these antibiotics can be mentioned.

The antibiotic within the meaning of the present invention can also be an antibiotic activatable via another bio-activation pathway than the aforementioned one.

EXPERIMENTAL SECTION

Synthesis Process(es)

$^1$H and $^{13}$C nuclear magnetic resonance spectra (NMR) were performed at ambient temperature on a Bruker™ DRX 300 MHz spectrometer. The chemical shifts are expressed in parts per million (ppm). The assignments have been performed using $^1$H and $^{13}$C one-dimensional (1D) or two-dimensional (2D) HSQC-COSY experiments. Mass spectra were performed on an LCMS mass spectrometer equipped with a triple quadripole system (Varian 1200ws) or on an LCMS Waters Alliance Micromass ZQ 2000 system. The commercial reagents and solvents were used without ulterior purification.

Flow Diagram of the Synthetic Process(es) for Compounds 1 to 3

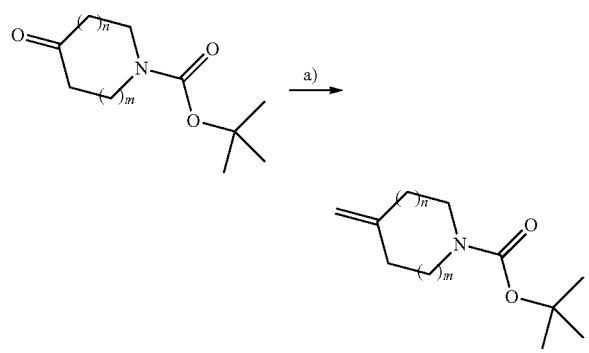

a) tBuOK, Et₂O, Ph₃(CH₃)P+,I-
1 (n=1 and m=1)
2 (n=0 and m=1)
3 (n=0 and m=0)

Synthesis of the intermediate products 1, 2 and 3. Potassium tert-butoxide (1.5 mmoles) is added to the suspension under argon, of triphenylmethylphosphonium iodide (1.5 mmoles) in anhydrous ether (2.0 mL). The mixture is refluxed for 1 h and then turns yellow. The ketonic compound is then added in portions. After 30 minutes of agitation at ambient temperature, the TLC analysis indicates that the reaction has been completed. The reaction medium is then hydrolyzed using distilled water (1 mL) and extracted twice using ether. The joint organic phases are dried on $MgSO_4$ and concentrated to dryness. The residue obtained is purified on a silica gel column (cyclohexane/ethyl acetate eluent) to give the expected product in the form of a colorless oil.

1-N-Boc-4-methylenepiperidine (1). $^1$H NMR (CDCl$_3$, 300 MHz) δ (ppm) 1.47 (s, 9H, CH$_3$ Boc), 2.18 (t, 4H, J=5.9 Hz, CH$_2$), 3.42 (t, 4H, J=5.8 Hz, CH$_2$N), 4.74 (s, 2H, =CH$_2$). 70% yield. [(M-tBu), H]$^+$ 142.1. Purity>95%.

1-N-Boc-3-methylenepyrrolidine (2). $^1$H NMR (CDCl$_3$, 300 MHz) δ (ppm) 1.48 (s, 9H, CH$_3$ Boc), 2.55 (t, 2H, J=7.2 Hz, CH$_2$), 3.48 (m, 2H, CH$_2$), 3.93 (m, 2H, CH$_2$), 4.98 (m, 2H, =CH$_2$). 83% yield. [(M-tBu), H]$^+$ 128.1. Purity>95%.

1-N-Boc-3-methyleneazetidine (3). $^1$H NMR (CDCl$_3$, 300 MHz) δ (ppm) 1.46 (s, 9H CH$_3$ Boc), 4.49 (t, 4H, J=2.7 Hz, CH$_2$), 4.99 (q, 2H, J=2.4 Hz, CH$_2$). 69% yield. [(M-tBu), H]$^+$ 114.3. Purity>95%.

Flow Diagram of the Synthetic Process(es) for Compounds 4, 5 and 10

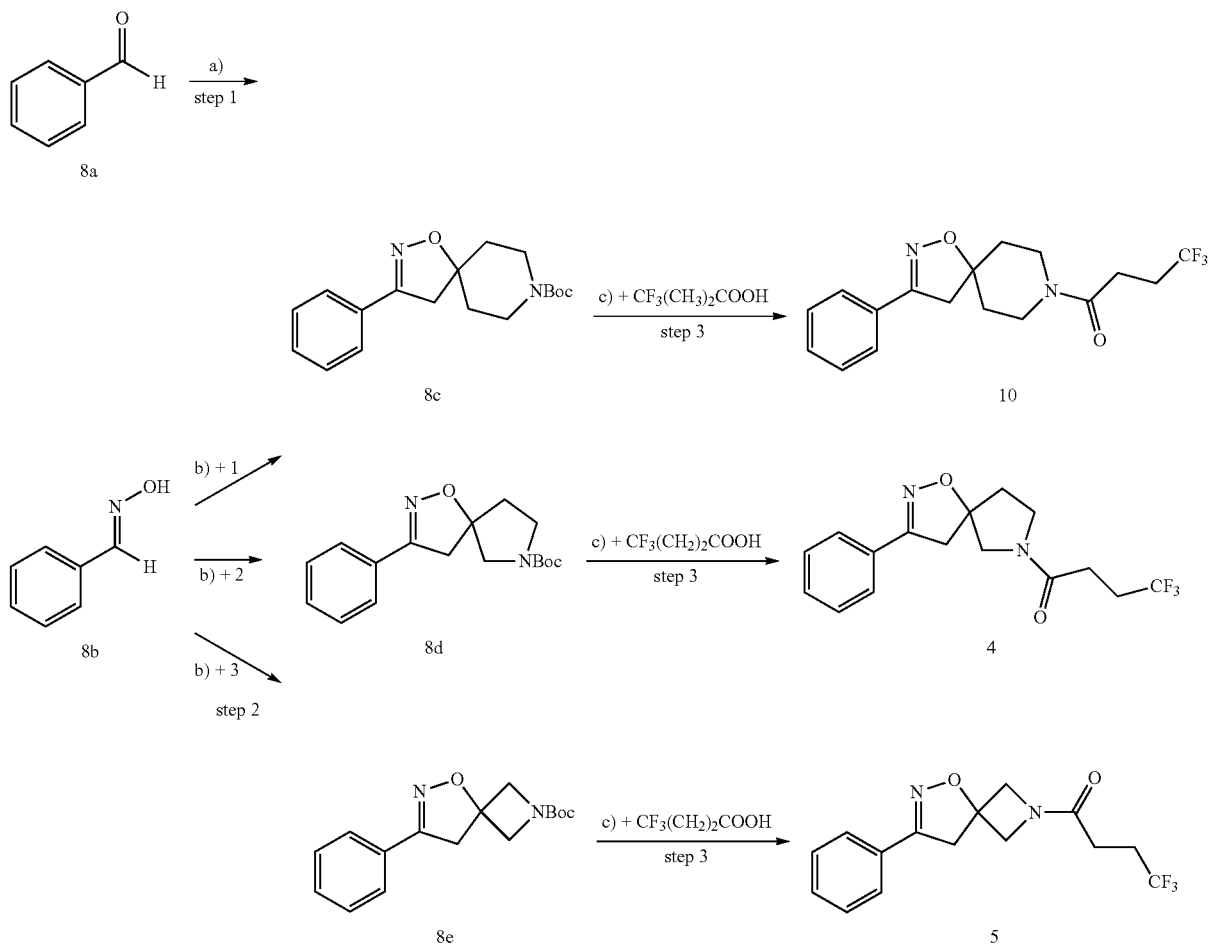

Flow Diagram of the Synthetic Process(es) for Compounds 8 to 9

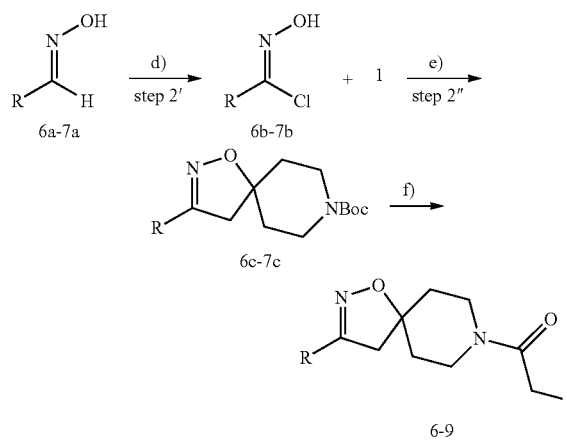

Flow Diagram of the Synthetic Process(es) for Compounds 11 to 59

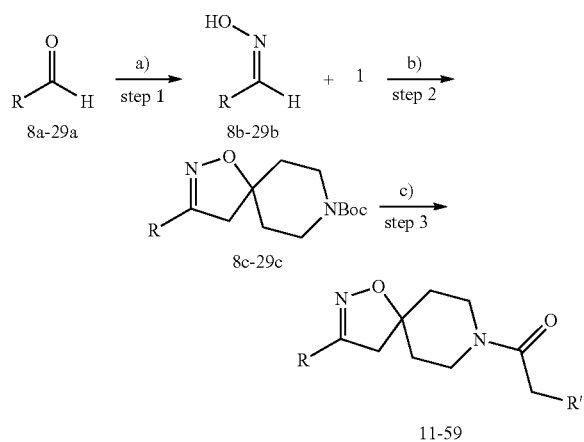

Operational conditions: (a) $NH_2OH.HCl$, $CH_2Cl_2$, pyridine, RT; (b) NaOCl 13%, $CH_2Cl_2$, 0° C. to RT: (c) (i) HCl (4M) in 1,4-dioxane, (ii) R'—$CO_2H$, HOBt, EDCl.HCl, DIEA, DMF; (d) NCS, DMF, RT, (e) 1-N-Boc-4-methylene-piperidine, $Et_3N$, THF, RT; (f) (i) HCl (4M) in 1,4-dioxane, (ii) $CF_3(CH_2)_2$—$CO_2H$, HOBt, EDCl.HCl, DIEA, DMF.

Step 1: oxime synthesis: Hydroxylamine hydrochloride (1 mmole) is added to the aldehyde solution (1 mmole) in dichloromethane (860 µL) and pyridine (80 µL). The mixture is then agitated at ambient temperature. The progress and the end of the reaction are followed via thin-layer chromatography (TLC). Dichloromethane is added, then the organic phase is washed using distilled water, dried on $MgSO_4$ and concentrated to dryness. The oxime thus obtained is used without any subsequent purification being necessary.

Step 2: process for synthesizing the intermediate products 8c to 29c. A solution of sodium hypochlorite (13% chlorine solution, 3.4 mL) is added to the oxime solution (1 mmole) and alkene 1, 2 or 3 (0.8 mmoles) in $CH_2Cl_2$ cooled to 0° C. The mixture is agitated at ambient temperature until the reaction is complete. The two phases are separated and the organic phase is then successively washed using 1N HCl (twice), a solution saturated with $NaHCO_3$ and brine before being evaporated under reduced pressure. If necessary, the spiroisoxazoline derivative obtained is purified using preparative HPLC or flash chromatography (cyclohexane/ethyl acetate eluent).

Step 2' and 2": process for the synthesis of the derivatives 6b-6c and 7b-7c. N-chloro-succinimide (1 mmole) is added to the oxime solution (1 mmole) in DMF (1.9 mL). After agitation during 1 h at ambient temperature (the LC/MS control showing the end of the reaction), the DMF is evaporated under reduced pressure. The obtained residue is taken up in $CH_2Cl_2$, then washed twice using brine. The organic phase is dried on $MgSO_4$ and concentrated to dryness. A triethylamine solution (2 mmoles) in THF (32 mL) is added drop-wise during 4 h to the solution of chloro-oxime and 1-N-Boc-4-methylene-piperidine (1.3 mmoles) in THF (32 mL). The reaction medium is agitated at ambient temperature. Triethylamine hydrochloride thus formed is eliminated by filtration and the THF is evaporated under reduced pressure. The residue obtained is taken up in dichloromethane and is washed successively using a solution of 1N HCl and brine. The organic phase is then dried on $MgSO_4$ and concentrated to dryness. The residue collected is purified on a silica gel column ($CH_2Cl_2$/EtOAc eluent).

Step 3: deprotection of the N-Boc group. A solution of 4N HCl in dioxane (2.2 mL) is added to the solution of N-Boc-amine (1 mmole) in dioxane (4.4 mL). The reaction medium is agitated at ambient temperature. Once the reaction is completed (followed by TLC), the precipitate formed is centrifuged on sintered glass and used without subsequent purification in the coupling step.

Coupling with carboxylic acids: A solution of carboxylic acid (1.5 mmoles), EDCl.HCl (1.5 mmoles), HOBt (0.5 mmoles) and diisopropylethyl amine (4 mmoles) in DMF is agitated at ambient temperature during 15 minutes. The spiroisoxazoline hydrochloride (1 mmole) is then added thereto. As the reaction will be completed after 2 h of agitation (followed by LC/MS), the solvent is evaporated under reduced pressure. The residue obtained is taken up in dichloromethane and is washed successively using 1N HCl (twice), a saturated solution of $NaHCO_3$ and brine. The organic phase is then dried on $MgSO_4$ and concentrated to dryness. The compound is then purified using preparative HPLC.

Evaluation of the Compounds' Activity

Potentiation of Ethionamide Cell Test

The test used makes it possible to ascertain that these compounds are capable of potentiating the bactericide activity of ethionamide on macrophages infected by *M. tuberculosis*. This test is a "High Content Screening" (HCS) or dense content screening test. HCS tests are performed on cell cultures that enable certain phenotypic features of a microorganism (e.g. a bacterium) in a given environment to be studied. The phenotypic changes observed can range from the increase (or decrease) of the production of certain marked proteins to the modification of the morphology of the microorganism under consideration. The method is described in the following publication: "Ethionamide Boosters: Synthesis, Biological Activity, and Structure-Activity Relationships of a Series of 1,2,4-Oxadiazole EthR Inhibitors", M. Flipo et al., Journal of Medicinal Chemistry, 2011, 54(8), 2994-3010.

This test aims to determine the ligand concentration necessary to potentiate ten times the activity of ethionamide (ETH).

To measure the ligand concentration necessary for potentiating ten times the activity of ETH, a constant concentration of ethionamide (0.1 μg/mL corresponding to $1/10^{th}$ of its $CMI_{99}$) is chosen. By varying the ligand concentration, the concentration necessary to inhibit 50% of the bacterial growth, i.e. the concentration necessary to potentiate ten times the activity of ethionamide, can be determined. This concentration will be denoted $EC_{50}$.

Measurement of the Solubility

40 μL of a 10 mM solution in DMSO of the sample are added to 1.96 mL MeOH or PBS at pH 7.4. The samples are then agitated during 24 h at RT, centrifuged during 5 min and then filtrated on filters of 0.45 μm pore size. 20 μL of each solution are then added to 180 μL MeOH and then analyzed by LC-MS. The solubility is determined as ratio of the surfaces of the mass signals PBS/MeOH.

Measured Biological Activities

Table I hereafter summarizes the formulas of the inventive compounds tested as well as the values of $EC_{50}$ experimentally measured according to the aforementioned protocol.

TABLE I

| No | Compound | NMR | $[MH]^+$ | $EC_{50}$ (μM) |
|----|----------|-----|----------|----------------|
| 4 | BDM_44636 326.32 g/mol | $^1$H (CD$_2$Cl$_2$, 300 MHz): δ (ppm) 2.22 (m, 1H), 2.52 (m, 5H), 3.48 (m, 2H), 3.61-3.98 (m, 4H), 7.47 (m, 3H), 7.70 (m, 2H). $^{13}$C (CD$_2$Cl$_2$, 75 MHz): δ (ppm) 26.6 and 27.1 (q, J = 2.9 Hz), 29.0 (q, J = 29.5 Hz), 35.6, 37.2, 41.2 and 41.6, 44.9, 45.5, 55.7, 56.5, 89.7 and 91.2, 126.5, 128.7. 129.1, 130.3, 127.6 (q, J = 271.1 Hz), 156.5 and 156.6, 167.9 and 168.2. $^{19}$F (CD$_2$Cl$_2$, 282 MHz): δ (ppm) −67.00, −66.98. | 327 | 0.53 |
| 5 | BDM_44635 312.29 g/mol | $^1$H (CD$_2$Cl$_2$, 300 MHz): δ (ppm) 2.26-2.56 (m, 4H), 3.65 (s, 2H), 4.21 and 4.34 (2d, 2H, J = 11.1 and 10.5 Hz), 4.32 and 4.50 (2d, 2H, J = 9.3 and 9.3 Hz), 7.46 (m, 3H), 7.68 (m, 2H). $^{13}$C (CD$_2$Cl$_2$, 75 MHz): δ (ppm) 24.3 (q, J = 3.1 Hz), 28.8 (q, J = 28.4 Hz), 44.5, 61.5, 63.7, 80.2, 126.6, 128.8, 130.5, 127.1 (q, J = 279.5 Hz), 156.8, 169.1. $^{19}$F (CD$_2$Cl$_2$, 282 MHz): δ (ppm) −37.12. | 313 | 0.11 |
| 6 | BDM_41774 346.37 g/mol | $^1$H (CDCl$_3$, 300 MHz): δ (ppm) 1.69 (m, 2H), 1.94 (m, 2H), 2.46 (m, 4H), 3.12 (s, 2H), 3.24 (m, 1H), 3.52 (m, 2H), 4.26 (m, 1H), 7.04 (q, 1H, J = 5.1 and 3.6 Hz), 7.16 (dd, 1H, J = 3.6 and 1.1 Hz), 7.38 (dd, 1H, J = 5.1 and 1.1 Hz). | 347 | 0.03 |
| 7 | BDM_41776 347.36 g/mol | $^1$H (CDCl$_3$, 300 MHz): δ (ppm) 1.72 (m, 2H), 1.95 (m, 2H), 2.45 (m, 4H), 3.29 (s, 2H), 3.33 (m, 1H), 3.58 (m, 2H), 4.15 (m, 1H), 7.41 (d, 1H, J = 3.2 Hz), 7.86 (d, 1H, J = 3.2 Hz). $^{13}$C (CDCl$_3$, 75 MHz): δ (ppm) 25.9, 29.6 (q, J = 29.1 Hz), 35.4, 36.2, 37.9, 39.0, 45.2, 85.7, 121.3, 127.1 (q, J = 274.0 Hz), 143.5, 153.8, 157.7, 168.0. | 348 | 0.04 |

TABLE I-continued

| No | Compound | NMR | [MH]+ | EC$_{50}$ (μM) |
|---|---|---|---|---|
| 8 | BDM_44783 | $^1$H (CD$_2$Cl$_2$, 300 MHz): δ (ppm) 0.91 (d, 6H, J = 6.6 Hz), 1.40-1.58 (m, 3H), 1.71 (m, 2H), 1.91 (m, 2H), 3.12 (s, 2H), 3.35 (m, 1H), 3.58 (m, 2H), 4.04 (m, 1H), 7.07 (m, 2H), 7.17 (m, 2H), 7.40 (m, 2H). | 321 | 0.13 |
| 9 | BDM_44780 | $^1$H (CDCl$_3$, 300 MHz): δ (ppm) 1.79 (m, 2H), 1.90 (m, 4H), 2.16 (m, 2H), 2.42 (t, 2H, J = 7.2 Hz), 3.29 (s, 2H), 3.33 (m, 1H), 3.58 (m, 2H), 4.03 (m, 1H), 7.45 (d, 1H, J = 3.2 Hz), 7.86 (d, 1H, J = 3.2 Hz). | 362 | 0.07 |
| 10 | BDM_41420 340.35 g/mol | $^1$H (CD$_2$Cl$_2$, 300 MHz): δ (ppm) 1.36-1.88 (m, 2H), 1.90-2.04 (m, 2H), 2.45-2.61 (m, 4H), 3.16 (s, 2H), 3.42 (m, 1H), 3.56 (m, 2H), 4.13 (m, 1H), 7.47 (m, 3H), 7.70 (m, 2H). $^{13}$C (CD$_2$Cl$_2$, 75 MHz): δ (ppm) 25.8, 29.5 (q, J = 39.1 Hz), 35.5 and 36.2, 39.4 and 42.6, 45.3, 84.1, 126.5, 128.7 and 130.0, 127.6 (q, J = 275.3 Hz), 156.4, 167.8. | 341 | 0.02 |
| 11 | BDM_41781 354.38 g/mol | $^1$H (CDCl$_3$, 300 MHz): δ (ppm) 1.69 (m, 2H), 1.94 (m, 2H), 2.38 (s, 3H), 2.45 (m, 4H), 3.10 (s, 2H), 3.25 (m, 1H), 3.53 (m, 2H), 4.26 (m, 1H), 7.19 (d, 2H, J = 7.9 Hz), 7.54 (d, 2H, J = 5.0 Hz). | 355 | 2.50 |
| 12 | BDM_41789 382.43 g/mol | $^1$H (CDCl$_3$, 300 MHz): δ (ppm) 1.25 (d, 6H, J = 6.9 Hz), 1.69 (m, 2H), 1.94 (m, 2H), 2.43 (m, 4H), 2.89 (qp, 1H, J = 13.8 and 6.9 Hz), 3.11 (s, 2H), 3.26 (m, 1H), 3.54 (m, 2H), 4.26 (m, 1H), 7.26 (d, 2H, J = 8.2 Hz), 7.56 (dt, 2H, J = 8.3 and 1.9 Hz). | 383 | ND |

TABLE I-continued

| No | Compound | NMR | [MH]+ | EC$_{50}$ (μM) |
|---|---|---|---|---|
| 13 | BDM_41793<br>396.46 g/mol | $^1$H (CDCl$_3$, 300 MHz): δ (ppm) 1.30 (s, 9H), 1.66 (m, 2H), 1.92 (m, 2H), 2.42 (m, 4H), 3.08 (s, 2H), 3.22 (m, 1H), 3.50 (m, 2H), 4.24 (m, 1H), 7.38 (d, 2H, J = 8.6 Hz), 7.54 (d, 2H, J = 8.6 Hz). | 397 | ND |
| 14 | BDM_41938<br>370.37 g/mol | $^1$H (CDCl$_3$, 300 MHz): δ (ppm) 1.66 (m, 2H), 1.94 (m, 2H), 2.40 (m, 4H), 3.22 (s, 2H), 3.25 (m, 1H), 3.52 (m, 2H), 3.84 (s, 3H), 4.23 (m, 1H), 6.91 (m, 2H), 7.35 (td, 1H, J = 7.5 and 1.7 Hz), 7.70 (dd, 1H, J = 7.7 and 1.7 Hz). | 371 | 0.02 |
| 15 | BDM_43097<br>370.37 g/mol | $^1$H (CD$_2$Cl$_2$, 300 MHz): δ (ppm) 1.71 (m, 2H), 1.94 (m, 2H), 2.55 (m, 4H), 3.14 (s, 2H), 3.38 (m, 1H), 3.58 (m, 2H), 3.85 (s, 3H), 4.17 (m, 1H), 6.99 (m, 1H), 7.21 (m, 2H), 7.35 (t, 1H, J = 7.8 Hz). | 371 | 0.29 |
| 16 | BDM_41935<br>370.37 g/mol | $^1$H (CDCl$_3$, 300 MHz): δ (ppm) 1.68 (m, 2H), 1.94 (m, 2H), 2.46 (m, 4H), 3.09 (s, 2H), 3.25 (m, 1H), 3.53 (m, 2H), 3.83 (s, 3H), 4.26 (m, 1H), 6.90 (m, 1H), 7.56 (m, 1H). | 371 | ND |
| 17 | BDM_43116<br>400.40 g/mol | $^1$H (CD$_2$Cl$_2$, 300 MHz): δ (ppm) 1.82 (m, 2H), 1.95 (m, 2H), 2.55 (m, 4H), 3.13 (s, 2H), 3.43 (m, 1H), 3.65 (m, 2H), 3.89 (s, 6H), 4.15 (m, 1H), 6.90 (d, 1H, J = 8.4 Hz), 7.07 (dd, 1H, J = 8.3 and 2.0 Hz), 7.35 (d, 1H, J = 1.9 Hz). | 401 | ND |

TABLE I-continued

| No | Compound | NMR | [MH]+ | EC$_{50}$ (μM) |
|---|---|---|---|---|
| 18 | BDM_41797<br>384.36 g/mol | $^1$H (CDCl$_3$, 300 MHz): δ (ppm) 1.69 (m, 2H), 1.95 (m, 2H), 2.48 (m, 4H), 3.08 (s, 2H), 3.25 (m, 1H), 3.54 (m, 2H), 4.27 (m, 1H), 6.02 (s, 2H), 6.81 (d, 1H, J = 8.1 Hz), 6.99 (dd, 1H, J = 8.1 and 1.7 Hz), 7.27 (d, 1H, J = 1.5 Hz). | 385 | 1.30 |
| 19 | BDM_41791<br>424.35 g/mol | $^1$H (CDCl$_3$, 300 MHz): δ (ppm) 1.70 (m, 2H), 1.94 (m, 2H), 2.45 (m, 4H), 3.10 (s, 2H), 3.24 (m, 1H), 3.53 (m, 2H), 4.26 (m, 1H), 7.24 (m, 2H), 7.66 (dt, 2H, J = 9.0 and 2.7 Hz). | 425 | <20 |
| 20 | BDM_41931<br>374.79 g/mol | $^1$H (CDCl$_3$, 300 MHz): δ (ppm) 1.71 (m, 2H), 2.01 (m, 2H), 2.42 (m, 4H), 3.22 (s, 2H), 3.28 (m, 1H), 3.55 (m, 2H), 4.27 (m, 1H), 7.28 (m, 3H), 7.61 (dd, 1H, J = 7.3 and 1.9 Hz). | 375 | 0.03 |
| 21 | BDM_41779<br>374.79 g/mol | $^1$H (CDCl$_3$, 300 MHz): δ (ppm) 1.69 (m, 2H), 1.95 (m, 2H), 2.46 (m, 4H), 3.09 (s, 2H), 3.24 (m, 1H), 3.53 (m, 2H), 4.26 (m, 1H), 7.35 (d, 2H, J = 13.2 Hz), 7.53 (d, 2H, J = 13.5 Hz). | 375 | 5.80 |
| 22 | BDM_41783<br>358.34 g/mol | $^1$H (CDCl$_3$, 300 MHz): δ (ppm) 1.69 (m, 2H), 1.95 (m, 2H), 2.43 (m, 4H), 3.10 (s, 2H), 3.24 (m, 1H), 3.53 (m, 2H), 4.27 (m, 1H), 7.05 (m, 2H), 7.60 (m, 2H). | 359 | 0.50 |

TABLE I-continued

| No | Compound | NMR | [MH]+ | EC$_{50}$ (μM) |
|---|---|---|---|---|
| 23 | BDM_41775<br>408.35 g/mol | $^1$H (CDCl$_3$, 300 MHz): δ (ppm) 1.72 (m, 2H), 1.97 (m, 2H), 2.47 (m, 4H), 3.15 (s, 2H), 3.27 (m, 1H), 3.55 (m, 2H), 4.28 (m, 1H), 7.52 (t, 1H, J = 7.7 Hz), 7.66 (d, 1H, J = 7.8 Hz), 7.85 (m, 1H). | 409 | 0.40 |
| 24 | BDM_41933<br>408.35 g/mol | $^1$H (CDCl$_3$, 300 MHz): δ (ppm) 1.72 (m, 2H), 1.98 (m, 2H), 2.47 (m, 4H), 3.14 (s, 2H), 3.27 (m, 1H), 3.55 (m, 2H), 4.29 (m, 1H), 7.66 (d, 1H, J = 8.3 Hz), 7.75 (d, 1H, J = 8.2 Hz). | 409 | <20 |
| 25 | BDM_43117<br>418.44 g/mol | $^1$H (CD$_2$Cl$_2$, 300 MHz): δ (ppm) 1.74 (m, 2H), 1.95 (m, 2H), 2.45 (m, 4H), 3.07 (s, 3H), 3.17 (s, 2H), 3.34 (m, 1H), 3.54 (m, 2H), 4.15 (m, 1H), 7.84 (ddt, 2H, J = 8.7 and 2.0 Hz), 7.96 (ddt, 2H, J = 8.6 and 1.8 Hz). | 419 | ND |
| 26 | BDM_41785<br>390.41 g/mol | $^1$H (CDCl$_3$, 300 MHz): δ (ppm) 1.73 (m, 2H), 1.99 (m, 2H), 2.47 (m, 4H), 3.24 (s, 2H), 3.28 (m, 1H), 3.55 (m, 2H), 4.28 (m, 1H), 7.48 (m, 2H), 7.81 (m, 4H), 7.94 (m, 1H). | 391 | ND |
| 27 | BDM_41795<br>346.40 g/mol | $^1$H (CDCl$_3$, 300 MHz): δ (ppm) 1.16 (m, 5H), 1.54 (m, 3H), 1.76 (m, 6H), 2.34 (m, 5H), 2.66 (s, 2H), 3.16 (m, 1H), 3.45 (m, 2H), 4.19 (m, 1H). | 347 | 0.08 |

TABLE I-continued

| No | Compound | NMR | [MH]$^+$ | EC$_{50}$ (μM) |
|----|----------|-----|----------|----------------|
| 28 | BDM_41787<br>332.37 g/mol | $^1$H (CDCl$_3$, 300 MHz): δ (ppm) 1.54 (m, 8H), 1.72 (m, 4H), 2.44 (m, 4H), 2.68 (s, 2H), 2.85 (m, 1H), 3.17 (m, 1H), 3.45 (m, 2H), 4.20 (m, 1H). | 333 | 0.08 |
| 29 | BDM_43100<br>354.38 g/mol | $^1$H (CD$_2$Cl$_2$, 300 MHz): δ (ppm) 1.54 (m, 2H), 1.77 (m, 2H), 2.44 (m, 4H), 3.25 (m, 1H), 3.54 (m, 2H), 3.68 (s, 2H), 4.02 (m, 1H), 7.24 (m, 5H). | 355 | 0.02 |
| 30 | BDM_41777<br>330.31 g/mol | $^1$H (CDCl$_3$, 300 MHz): δ (ppm) 1.68 (m, 2H), 1.93 (m, 2H), 2.44 (m, 4H), 3.08 (s, 2H), 3.25 (m, 1H), 3.53 (m, 2H), 4.24 (m, 1H), 6.84 (m, 1H), 6.70 (dd, 1H, J = 3.4 and 0.6 Hz), 7.51 (m, 1H). | 331 | 0.05 |
| 31 | BDM_41778<br>341.34 g/mol | $^1$H (CDCl$_3$, 300 MHz): δ (ppm) 1.72 (m, 2H), 1.94 (m, 2H), 2.40 (m, 4H), 3.29 (s, 2H), 3.38 (m, 1H), 3.48 (m, 2H), 4.11 (m, 1H), 7.28 (m, 1H), 7.70 (td, 1H, J = 7.6 and 1.8 Hz), 8.00 (dt, 1H, J = 8.0 and 1.1 Hz), 8.58 (m, 1H). | 342 | 0.15 |
| 32 | BDM_41418 | $^1$H (CD$_2$Cl$_2$, 300 MHz): δ (ppm) 0.82 (d, 6H, J = 6.3 Hz), 1.36-1.45 (m, 2H), 1.56 (m, 1H), 1.71 (m, 2H), 1.87 (m, 2H), 3.02 (s, 2H), 3.27 (m, 1H), 3.42 (m, 2H), 3.95 (m, 1H), 7.33 (m, 3H), 7.55 (m, 2H). | 315 | 5.00 |

TABLE I-continued

| No | Compound | NMR | [MH]+ | EC$_{50}$ (μM) |
|---|---|---|---|---|
| 33 | BDM_41796 | $^1$H (CDCl$_3$): δ (ppm) 0.90 (d, 6H, J = 6.28 Hz), 1.24 (m, 3H), 1.43 (m, 5H), 1.70 (m, 5H), 1.91 (m, 2H), 2.02 (m, 2H), 2.31 (m, 2H), 2.71 (m, 1H), 2.81 (m, 1H), 3.10 (m, 2H), 3.87 (m, 1H), 4.47 (m, 1H). | 334 | ND |
| 34 | BDM_41788 | $^1$H (CDCl$_3$): δ (ppm) 0.90 (d, 6H, J = 6.29 Hz), 1.47 (m, 3H), 1.63 (m, 8H), 1.91 (m, 4H), 2.30 (m, 2H), 2.83 (m, 1H), 3.10 (m, 3H), 3.87 (m, 1H), 4.48 (m, 1H). | 320 | ND |
| 35 | BDM_43118 | $^1$H (CD$_2$Cl$_2$): δ (ppm) 0.93 (d, 6H, J = 6.40 Hz), 1.48 (m, 3H), 1.66 (m, 2H), 1.84 (m, 2H), 2.33 (m, 2H), 3.07 (s, 3H), 3.16 (s, 2H), 3.35 (m, 1H), 3.55 (m, 2H), 4.08 (m, 1H), 7.84 (ddt, 2H, J = 8.64 Hz, J = 1.98 Hz), 7.96 (ddt, 2H, J = 8.63 Hz, J = 1.81 Hz). | 393 | ND |
| 36 | BDM_41780 | $^1$H (CDCl$_3$): δ (ppm) 0.89 (d, 6H, J = 6.26 Hz), 1.47 (m, 3H), 1.62 (m, 2H), 1.91 (m, 2H), 2.30 (m, 2H), 3.06 (s, 2H), 3.25 (m, 1H), 3.50 (m, 2H), 4.19 (m, 1H), 7.33 (m, 2H), 7.53 (m, 2H). | 349 | ND |
| 37 | BDM_41782 | $^1$H (CDCl$_3$): δ (ppm) 0.93 (d, 6H, J = 6.28 Hz), 1.51 (m, 3H), 1.25 (m, 2H), 1.94 (m, 2H), 2.31 (m, 2H), 2.39 (s, 3H), 3.11 (s, 2H), 3.29 (m, 1H), 3.54 (m, 2H), 4.21 (m, 1H), 7.21 (d, 2H, J = 7.97 Hz), 7.54 (d, 2H, J = 8.14 Hz). | 329 | ND |
| 38 | BDM_41784 | $^1$H (CDCl$_3$): δ (ppm) 0.90 (d, 6H, J = 6.28 Hz), 1.48 (m, 3H), 1.64 (m, 2H), 1.92 (m, 2H), 2.32 (m, 2H), 3.08 (s, 2H), 3.26 (m, 1H), 3.52 (m, 2H), 4.20 (m, 1H), 7.06 (m, 2H), 7.60 (m, 2H). | 333 | ND |

TABLE I-continued

| No | Compound | NMR | [MH]+ | EC$_{50}$ (μM) |
|---|---|---|---|---|
| 39 | BDM_41786 | $^1$H (CDCl$_3$): δ (ppm) 0.91 (d, 6H, J = 6.27 Hz), 1.49 (m, 3H), 1.64 (m, 2H), 1.95 (m, 2H), 2.33 (m, 2H), 3.22 (s, 2H), 3.30 (m, 1H), 3.54 (m, 2H), 4.20 (m, 1H), 7.47 (m, 2H), 7.82 (m, 4H), 7.94 (m, 1H). | 365 | ND |
| 40 | BDM_41790 | $^1$H (CDCl$_3$): δ (ppm) 0.93 (d, 6H, J = 6.28 Hz), 1.26 (d, 6H, J = 6.91 Hz), 1.49 (m, 3H), 1.66 (m, 2H), 1.94 (m, 2H), 2.34 (m, 2H), 2.90 (qp, 1H, J = 13.79 Hz, J = 6.90 Hz), 3.11 (s, 2H), 3.29 (m, 1H), 3.54 (m, 2H), 4.23 (m, 1H), 7.27 (d, 2H, J = 8.21 Hz), 7.58 (d, 2H, J = 8.32 Hz). | 357 | ND |
| 41 | BDM_41792 | $^1$H (CDCl$_3$): δ (ppm) 0.93 (d, 6H, J = 6.28 Hz), 1.51 (m, 3H), 1.66 (m, 2H), 1.95 (m, 2H), 2.34 (m, 2H), 3.11 (s, 2H), 3.28 (m, 1H), 3.54 (m, 2H), 4.25 (m, 1H), 7.28 (d, 2H, J = 7.98 Hz), 7.67 (dt, 2H, J = 6.85 Hz, J = 2.02 Hz). | 399 | ND |
| 42 | BDM_41794 | $^1$H (CDCl$_3$): δ (ppm) 0.91 (d, 6H, J = 6.27 Hz), 1.32 (s, 9H), 1.48 (m, 3H), 1.62 (m, 2H), 1.92 (m, 2H), 2.32 (m, 2H), 3.09 (s, 2H), 3.26 (m, 1H), 3.53 (m, 2H), 4.21 (m, 1H), 7.41 (d, 2H, J = 8.48 Hz), 7.57 (d, 2H, J = 8.40 Hz). | 371 | ND |
| 43 | BDM_41796 | $^1$H (CDCl$_3$): δ (ppm) 0.88 (d, 6H, J = 6.30 Hz), 1.23 (m, 5H), 1.45 (m, 6H), 1.69 (m, 6H), 2.28 (m, 3H), 2.64 (s, 2H), 3.17 (m, 1H), 3.43 (m, 2H), 4.13 (m, 1H). | 321 | ND |
| 44 | BDM_41798 | $^1$H (CDCl$_3$): δ (ppm) 0.93 (d, 6H, J = 6.30 Hz), 1.49 (m, 2H), 1.66 (m, 2H), 1.78 (m, 2H), 1.94 (m, 2H), 2.34 (m, 2H), 3.07 (s, 2H), 3.27 (m, 1H), 3.54 (m, 2H), 4.22 (m, 1H), 6.02 (s, 2H), 6.81 (d, 1H, J = 8.30 Hz), 6.99 (dd, 1H, J = 8.06 Hz, J = 1.70 Hz), 7.28 (d, 1H, J = 1.64 Hz). | 359 | ND |

TABLE I-continued

| No | Compound | NMR | [MH]+ | EC$_{50}$ (μM) |
|---|---|---|---|---|
| 45 | BDM_41799 | $^1$H (CDCl$_3$): δ (ppm) 0.91 (d, 6H, J = 6.29 Hz), 1.48 (m, 3H), 1.64 (m, 2H), 1.93 (m, 2H), 2.33 (m, 2H), 3.28 (s, 2H), 3.42 (m, 1H), 3.59 (m, 2H), 4.04 (m, 1H), 7.27 (m, 1H), 7.70 (td, 1H, J = 7.67 Hz, J = 1.77 Hz), 8.00 (dt, 1H, J = 7.99 Hz, J = 1.03 Hz), 8.58 (m, 1H). | 316 | 1.30 |
| 46 | BDM_41932 | $^1$H (CDCl$_3$): δ (ppm) 0.92 (d, 6H, J = 6.29 Hz), 1.49 (m, 3H), 1.65 (m, 2H), 1.98 (m, 2H), 2.33 (m, 2H), 3.27 (s, 2H), 3.30 (m, 1H), 3.54 (m, 2H), 4.19 (m, 1H), 7.27 (m, 3H), 7.61 (dd, 1H, J = 7.29 Hz, J = 1.81 Hz). | 349 | 1.30 |
| 47 | BDM_41934 | $^1$H (CDCl$_3$): δ (ppm) 0.90 (d, 6H, J = 6.26 Hz), 1.48 (m, 3H), 1.70 (m, 2H), 1.93 (m, 2H), 2.31 (m, 2H), 3.10 (s, 2H), 3.26 (m, 1H), 3.49 (m, 2H), 4.21 (m, 1H), 7.63 (d, 1H, J = 8.29 Hz), 7.73 (d, 1H, J = 8.24 Hz). | 383 | ND |
| 48 | BDM_41936 | $^1$H (CDCl$_3$): δ (ppm) 0.90 (d, 6H, J = 6.26 Hz), 1.48 (m, 3H), 1.61 (m, 2H), 1.91 (m, 2H), 2.31 (m, 2H), 3.07 (s, 2H), 3.26 (m, 1H), 3.51 (m, 2H), 3.82 (s, 3H), 4.19 (m, 1H), 6.89 (m, 1H), 7.55 (m, 1H). | 345 | ND |
| 49 | BDM_41939 | $^1$H (CDCl$_3$): δ (ppm) 0.91 (d, 6H, J = 6.30 Hz), 1.48 (m, 3H), 1.62 (m, 2H), 1.92 (m, 2H), 2.32 (m, 2H), 3.22 (s, 2H), 3.27 (m, 1H), 3.57 (m, 2H), 3.85 (s, 3H), 4.18 (m, 1H), 6.92 (m, 2H), 7.35 (td, 1H, J = 7.46 Hz, J = 1.74 Hz), 7.70 (dd, 1H, J = 7.68 Hz, J = 1.72 Hz). | 345 | 0.63 |
| 50 | BDM_43103 | $^1$H (CD$_2$Cl$_2$): δ (ppm) 1.72 (m, 2H), 1.86 (m, 4H), 2.15 (m, 2H), 2.43 (m, 2H), 3.29 (s, 2H), 3.34 (m, 1H), 3.52 (m, 2H), 4.10 (m, 1H), 7.33 (m, 2H), 7.46 (m, 1H), 7.61 (m, 1H). | 389 | 0.77 |
| 51 | BDM_41941 | $^1$H (MeOD): δ (ppm) 1.74 (m, 6H), 2.13 (m, 2H), 2.52 (t, 2H, J = 7.20 Hz), 3.26 (s, 2H), 3.40 (m, 1H), 3.49 (m, 1H), 3.65 (m, 1H), 3.99 (m, 1H), 7.40 (m, 3H), 7.65 (m, 2H). | 355 | 1.00 |

TABLE I-continued

| No | Compound | NMR | [MH]+ | EC50 (μM) |
|---|---|---|---|---|
| 52 | BDM_43119 | ¹H (CD₂Cl₂): δ (ppm) 1.75 (m, 2H), 1.86 (m, 4H), 2.15 (m, 2H), 2.42 (m, 2H), 3.07 (s, 3H), 3.16 (s, 2H), 3.34 (m, 1H), 3.52 (m, 2H), 4.11 (m, 1H), 7.85 (ddt, 2H, J = 8.65 Hz, J = 1.94 Hz), 7.97 (ddt, 2H, J = 8.65 Hz, J = 1.72 Hz). | 433 | <20 |
| 53 | BDM_43092 | ¹H (CD₂Cl₂): δ (ppm) 1.72 (m, 2H), 1.94 (m, 2H), 3.14 (s, 2H), 3.35 (m, 1H), 3.59 (m, 1H), 3.67 (m, 1H), 4.13 (m, 1H), 4.73 (d, 1H, J = 3.80 Hz), 6.95 (m, 3H), 7.30 (m, 2H), 7.42 (m, 3H), 7.46 (m, 2H). | 351 | <20 |
| 54 | BDM_43113 | ¹H (CD₂Cl₂): δ (ppm) 1.76 (m, 1H), 1.85 (m, 3H), 3.13 (s, 3H), 3.16 (s, 2H), 3.31 (m, 1H), 3.62 (m, 1H), 3.76 (m, 1H), 4.05 (m, 2H), 4.27 (m, 1H), 7.42 (m, 3H), 7.64 (m, 2H). | 337 | <20 |
| 55 | BDM_43114 | ¹H (CD₂Cl₂): δ (ppm) 1.49 (m, 1H), 1.69 (m, 2H), 1.89 (m, 1H), 3.03 (d, 2H, J = 3.90 Hz), 3.36 (m, 1H), 3.52 (m, 2H), 4.10 (m, 1H), 7.25 (m, 3H), 7.33 (m, 2H), 7.41 (m, 3H), 7.63 (m, 2H). | 335 | <20 |
| 56 | BDM_43095 | ¹H (CD₂Cl₂): δ (ppm) 1.09 (m, 3H), 1.52 (m, 10H), 2.18 (m, 1H), 2.37 (m, 2H), 3.14 (s, 2H), 3.35 (m, 1H), 3.54 (m, 2H), 4.04 (m, 1H), 7.41 (m, 3H), 7.64 (m, 2H). | 327 | <20 |
| 57 | BDM_43102 | ¹H (CD₂Cl₂): δ (ppm) 1.42 (m, 1H), 1.72 (m, 2H), 1.91 (m, 2H), 2.11 (m, 1H), 2.23 (m, 5H), 3.15 (s, 2H), 3.37 (m, 1H), 3.54 (m, 2H), 4.09 (m, 1H), 5.72 (m, 1H), 5.78 (m, 1H), 7.42 (m, 3H), 7.65 (m, 2H). | 325 | <20 |

TABLE I-continued

| No | Compound | NMR | [MH]+ | EC$_{50}$ (μM) |
|---|---|---|---|---|
| 58 | BDM_43259 | $^1$H (CD$_2$Cl$_2$): δ (ppm) 1.59 (m, 2H), 1.87 (m, 2H), 3.11 (s, 2H), 3.35 (m, 1H), 3.57 (m, 2H), 3.94 (d, 2H, J = 2.40 Hz), 4.13 (m, 1H), 6.92 (m, 1H), 6.97 (dd, 1H, J = 5.12 Hz, J = 3.47 Hz), 7.24 (dd, 1H, J = 5.20 Hz, J = 1.14 Hz), 7.41 (m, 3H), 7.64 (m, 2H). | 341 | <20 |
| 59 | BDM_43104 | $^1$H (CD$_2$Cl$_2$): δ (ppm) 1.54 (m, 1H), 1.69 (m, 1H), 2.65 (m, 2H), 2.92 (m, 2H), 3.11 (s, 2H), 3.33 (m, 1H), 3.48 (m, 2H), 4.10 (m, 1H), 7.20 (m, 5H), 7.35 (m, 3H), 7.64 (m, 2H). | 349 | 1.00 |

By way of example of measured solubility, compound 10 (80DM41420) exhibits a solubility equal to 150 μM measured according to the aforementioned protocol.

The invention claimed is:

1. A compound of formula (I):

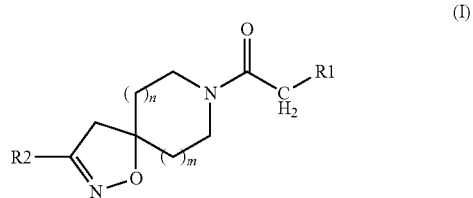

in which:
m is 0 or 1;
n is 0 or 1;
R1 is selected from the group consisting of: —CH$_2$CF$_3$ and —(CH$_2$)$_2$CF$_3$;
R2 is selected from the group consisting of: phenyl; benzyl optionally substituted by Cl or F; naphtanlenyl; phenyl substituted by linear or branched C1-C4 alkyl; phenyl substituted by linear or branched C1-C4 alkyl substituted by fluorine; phenyl substituted by one or more substituent selected from OCH$_3$, OCF$_3$, Cl, F, CH$_3$SO$_2$ and CF$_3$; phenyl having two consecutive carbon atoms substituted by —O—CH—O—; cyclopropyl; cyclobutyl; cyclopentyl; cyclohexyl; and a five- or six-membered hetercycle comprising one or more heteroatoms selected from S, N and O.

2. The compound according to claim 1, wherein m is 1 and n is 1.

3. The compound according to claim 1, wherein R1 is —CH$_2$CF$_3$.

4. The compound according to claim 1, wherein R2 is phenyl or phenyl substituted in ortho position by OCH$_3$, OCF$_3$, Cl, F or CF$_3$.

5. The compound according to claim 1, wherein R2 is a five- or six-membered heterocycle comprising one or more heteroatoms selected from S, N and O, and wherein one heteroatom is adjacent to the heterocycle atom bound to the carbon atom in alpha position relative to the nitrogen atom of the cycle

of formula (I).

6. The compound according to claim 1, wherein R2 is

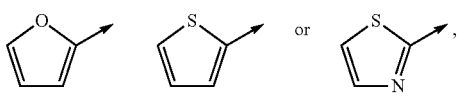

and wherein the arrow indicates the bond to the carbon atom in alpha position relative to the nitrogen atom of the cycle

of formula (I).

7. The compound according to claim 1, wherein R2 is selected from

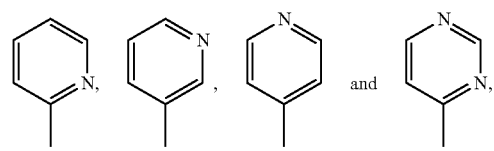

and wherein the bond indicates the bond to the carbon atom in alpha position relative to the nitrogen atom of the cycle

of formula (I).
8. The compound according to claim 1, which is selected from the group consisting of:
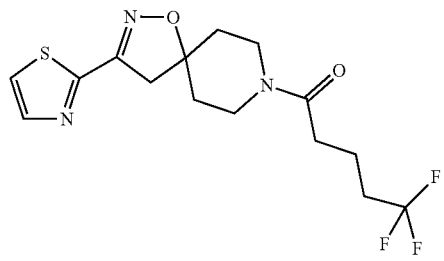
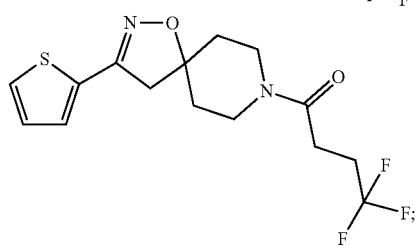
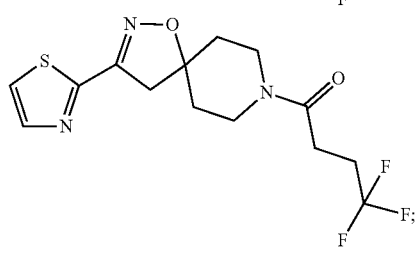
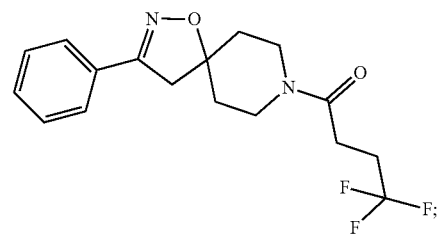
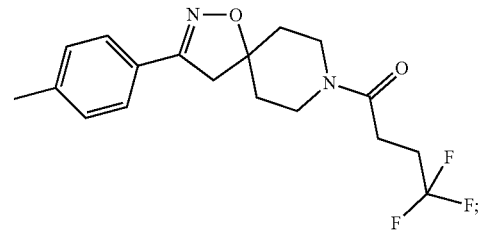
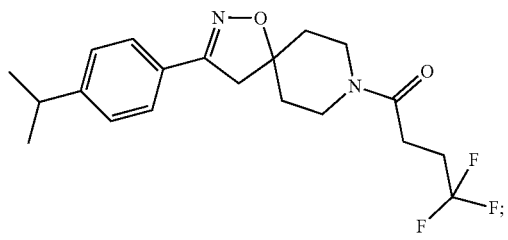
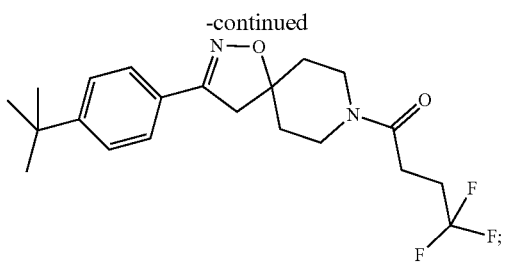

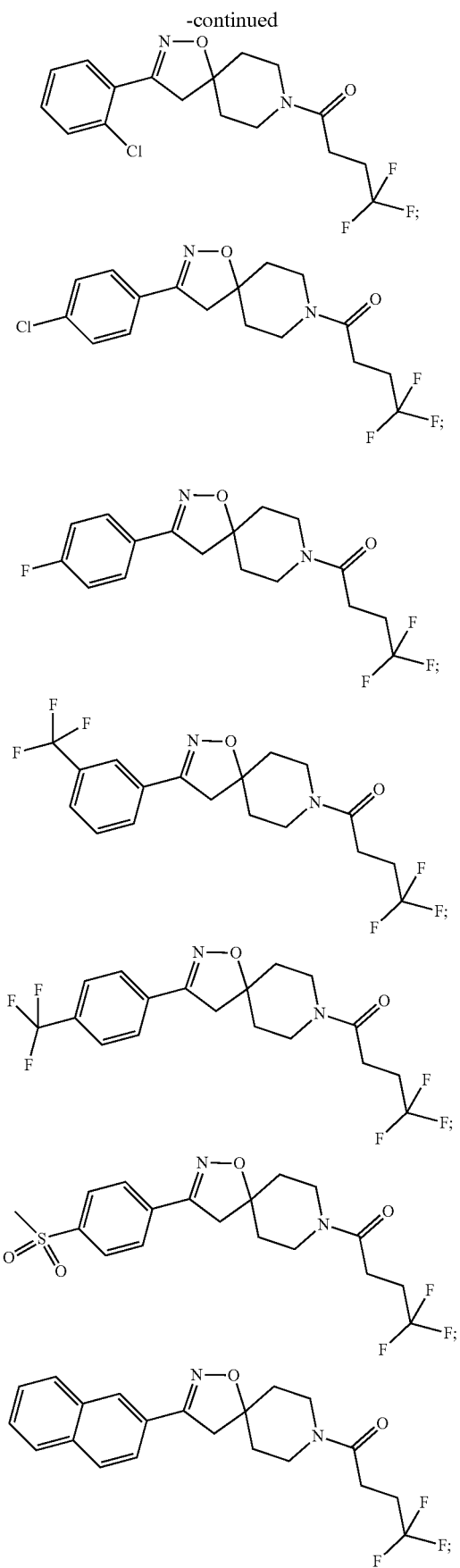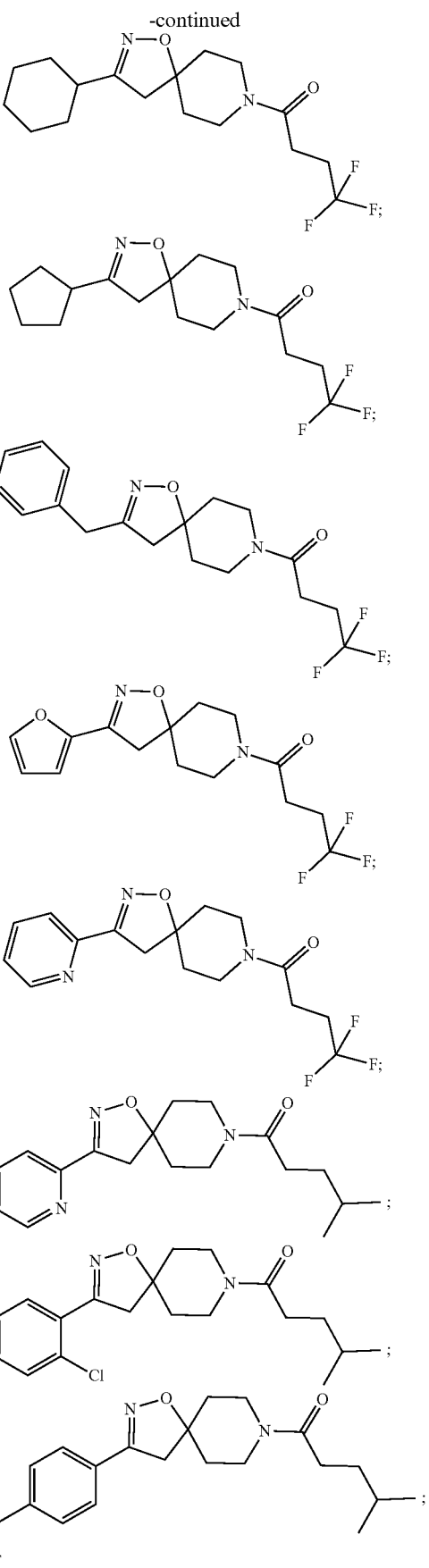

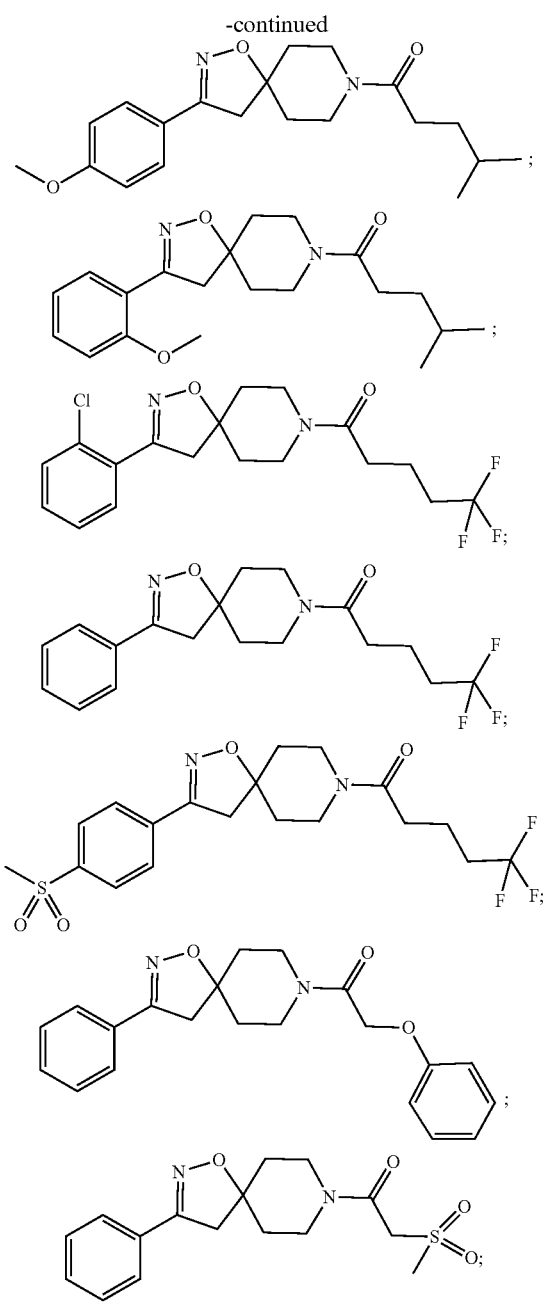

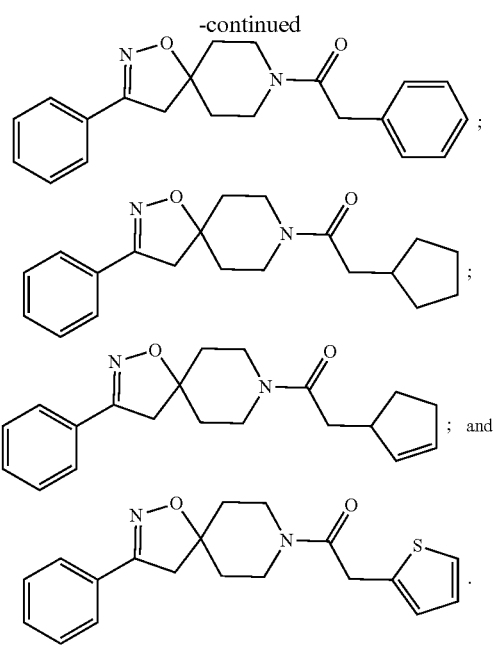

9. A method of treatment of bacterial and mycobacterial infections comprising administering to a patient in need thereof an effective amount of a compound of claim 1.

10. A method of treatment of tuberculosis, leprosy and atypical mycobacterial infections comprising administering to a patient in need thereof an effective amount of a compound of claim 1.

11. A pharmaceutical composition comprising as active ingredient a compound according to claim 1 and a pharmaceutically acceptable excipient.

12. The pharmaceutical composition according to claim 11 further comprising an antibiotic active against bacteria and/or mycobacteria.

13. The pharmaceutical composition according to claim 11 further comprising an antibiotic chosen from ethionamide, prothionamide, isoxyl and thiacetazone.

14. A method of treatment of tuberculosis, leprosy and atypical mycobacterial infections comprising administering to a patient in need thereof an effective amount of a compound of claim 1 and an effective amount of an antibiotic selected from ethionamide, prothionamide, isoxyl and thiacetazone.

15. The compound according to claim 1, wherein R1 is —(CH$_2$)$_2$CF$_3$.

* * * * *